United States Patent [19]

Kühle et al.

[11] Patent Number: 4,547,517
[45] Date of Patent: Oct. 15, 1985

[54] MICROBICIDAL N-SULPHENYLATED HYDANTOINS

[75] Inventors: Engelbert Kühle, Bergisch Gladbach; Wilfried Paulus; Hermann Genth, both of Krefeld; Paul Reinecke, Leverkusen; Hans-Jürgen Rosslenbroich, Monheim, all of Fed. Rep. of Germany

[73] Assignee: Bayer Aktiengesellschaft, Leverkusen, Fed. Rep. of Germany

[21] Appl. No.: 579,844

[22] Filed: Feb. 13, 1984

[30] Foreign Application Priority Data

Feb. 16, 1983 [DE] Fed. Rep. of Germany ....... 3305203

[51] Int. Cl.⁴ .................. A61K 31/415; C07D 233/82
[52] U.S. Cl. .................................... 514/390; 548/308; 548/311
[58] Field of Search ................... 548/311; 424/273 R

[56] References Cited

FOREIGN PATENT DOCUMENTS 1168914  4/1964  Fed. Rep. of Germany ...... 548/311
2441601  3/1975  Fed. Rep. of Germany ...... 548/311
3222523  12/1983  Fed. Rep. of Germany ...... 548/311

Primary Examiner—Richard A. Schwartz
Attorney, Agent, or Firm—Sprung, Horn, Kramer & Woods

[57] ABSTRACT

The new hydantoins of the formula

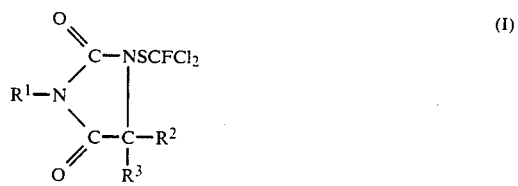

in which
R$^1$ denotes an optionally substituted alkyl, alkenyl, cycloalkyl or aralkyl radical and
R$^2$ and R$^3$ are identical or different and denote hydrogen, alkyl or alkenyl or are linked to form a cycloalkyl radical, can be prepared by reacting a corresponding hydantoin with dichlorofluoromethanesulphenyl chloride. The new compounds can be used as active compounds in microbicidal agents.

22 Claims, No Drawings

MICROBICIDAL N-SULPHENYLATED HYDANTOINS

The invention relates to new N-sulphenylated hydantoins, a process for their preparation and their use in microbicidal agents.

The use of some N-(trihalogenomethylthio) compounds for preserving industrial materials from microbial degradation is known (U.S. Pat. No. 2,553,770; Journ. Agr. Food Chem. 14, 365 (1966) and Fette, Seifen, Anstrichmittel 68, 272 (1966)). However, problems sometimes occur when they are used, since the known agents have a poor solubility in paints and impregnating agents.

New N-sulphenylated hydantoins of the formula

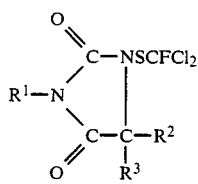

(I)

in which
R$^1$ denotes an optionally substituted alkyl, alkenyl, cycloalkyl or aralkyl radical and
R$^2$ and R$^3$ are identical or different and denote hydrogen, alkyl or alkenyl or are linked to form a cycloalkyl radical,
have now been found.

In addition to an outstanding microbicidal action, the new N-sulphenylated hydantoins have a good solubility in organic solvents and are particularly suitable for preserving industrial materials from microbial decomposition or destruction and in plant protection.

According to the invention, alkyl in general denotes a straight-chain or branched hydrocarbon radical with 1 to 12, preferably 1 to 8, carbon atoms. Examples which may be mentioned are methyl, ethyl, isopropyl, butyl, neopentyl, hexyl and octyl.

According to the invention, alkenyl in general denotes a straight-chain or branched unsaturated hydrocarbon radical with 2 to 12, preferably 3 to 8, carbon atoms and one or two, preferably one, double bond. Allyl, crotonyl and isooctenyl may be mentioned as examples.

According to the invention, cycloalkyl in general denotes a cyclic hydrocarbon radical with 5 to 12, preferably 5 to 8, carbon atoms. Examples which may be mentioned are: cyclopentyl, cyclohexyl, cycloheptyl and cyclooctyl.

Aralkyl in general denotes a radical comprising an aromatic and an aliphatic part, which consists of 6 to 10 carbon atoms in the aromatic part, preferably phenyl, and of 1 to about 6 carbon atoms in the aliphatic part. The following aralkyl radicals may be mentioned as examples: benzyl, 2-methylbenzyl, 2-phenethyl and 1-phenethyl.

The alkyl, alkenyl, cycloalkyl and aralkyl radicals can carry one or more, preferably 1 to 3 and in particular 1 or 2, identical or different substituents. Examples of substituents which may be mentioned are: alkyl with preferably 1 to 4, in particular 1 or 2, carbon atoms, such as methyl, ethyl and n- and iso-propyl; and halogen, preferably fluorine, chlorine, bromine and iodine, in particular chlorine and bromine; the alkyl radicals can also be interrupted by a hetero-atom, such as oxygen or sulphur.

The following sulphenylated hydantoins may be mentioned specifically: the 1-(dichlorofluoromethylmercapto) derivatives of 3-methyl-, 3-ethyl-, 3-isopropyl-, 3-methoxyethyl-, 3-ethylmercaptoethyl-, 3-tert.butyl-, 3-neopentyl-, 3-cyclopentyl-, 3-(4-methylcyclohexyl)-, 3(4-chlorobenzyl)-, 3(3-chlorophenethyl)-, 3,5,5-trimethyl-, 3-cyclohexyl-5,5-dimethyl-, 3-cyclohexyldiethyl- and 3-cyclohexyl-5-butylhydantoin.

A process has also been found for the preparation of N-sulphenylated hydantoins, which is characterised in that hydantoins of the formula

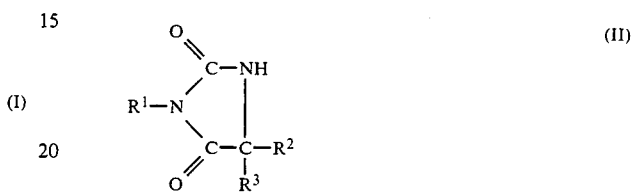

(II)

in which R$^1$, R$^2$ and R$^3$ have the abovementioned meanings, are reacted with dichlorofluoromethanesulphenyl chloride of the formula $$FCl_2CSCl \qquad (III)$$

in the presence of a diluent and an acid-binding agent.

The process according to the invention can be illustrated by the following equation:

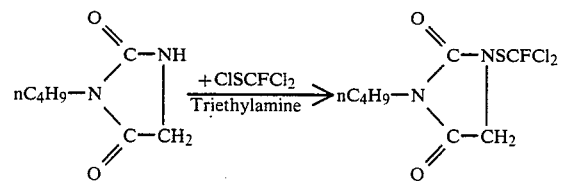

The hydantoins to be used for the process according to the invention are known per se and can be prepared in a manner which is known per se, for example by (a) reacting isocyanates with aminoacetic acid and then cyclising the addition product by dehydration, or (b) reacting isocyanate with α-aminonitrile and then cyclising the addition product by heating with concentrated hydrochloric acid and hydrolysing the cyclisation product (CA 55, 27277 a (1961)).

Dichlorofluoromethanesulphenyl chloride is also known (Ang. Chem. 76, 807 (1964)). Possible diluents for carrying out the process according to the invention are all the inert organic solvents. These include, preferably, hydrocarbons, such as toluene, chlorohydrocarbons, such as chlorobenzene, and ethers, such as dioxane. However, the reaction can also be carried out in water.

Tertiary amines and alkali metal hydroxides or alkali metal carbonates can be used as the acid-binding agents.

Examples of tertiary amines are compounds of the formula

(IV)

in which R$^7$, R$^8$ and R$^9$ are identical or different and represent lower alkyl (C$_1$ to about C$_6$).

The following tertiary amines may be mentioned as examples: trimethylamine, triethylamine and dimethylbenzylamine.

Alkali metal hydroxides and alkali metal carbonates are essentially sodium hydroxide, potassium hydroxide, sodium carbonate and potassium carbonate.

The process according to the invention is in general carried out in the temperature range from 0° to 100° C., preferably from 20° to 50° C.

The process according to the invention is in general carried out under normal pressure. However, it is also possible to carry out the process under an increased or reduced pressure.

In carrying out the process according to the invention, 1 to 3, preferably 1 to 1.1, mol of the dichlorofluoromethanesulphenyl chloride are in general employed per mol of the corresponding hydantoin.

The process according to the invention can in general be carried out as follows:

The hydantoin is dissolved in the diluent, with addition of the acid-binding agent, and the dichlorofluoromethanesulphenyl chloride is added. The reaction mixture is kept within the temperature range according to the invention for the reaction. After the acid-binding agent has been separated off, the solution is concentrated and the reaction product is separated off.

The N-sulphenylated hydantoins according to the invention are active compounds for combating microorganisms in the preservation of materials and plant protection. According to the invention, preservation of materials is understood as meaning the preservation of industrial materials from change or destruction by microorganisms.

Industrial raw materials in the context of the present invention are products which do not themselves occur in nature but are manufactured from naturally occurring or synthetic starting materials. The products to be preserved in the context of the present invention are industrial materials which can be decomposed by microorganisms, in general non-living things.

Examples of industrial materials which are to be preserved from microbial change or destruction by the active compounds according to the invention are adhesives, sizes, paper and cardboard, textiles, leather, wood, paints and articles made of plastic which can be attacked and decomposed by microorganisms. Components of production plants, such as, for example, cooling water and cooling lubricant circulations, the functioning of which can be impaired by microorganisms, may also be mentioned in the context of materials to be preserved. The active compounds according to the invention can preferably be used for the preservation of wood or paints.

Examples of microorganisms which can cause degradation of or a change in industrial materials are bacteria, fungi, yeast, algae and slime organisms. The active compounds according to the invention preferably act against moulds, fungi which discolour wood and fungi which destroy wood (Basidiomycetes), and against slime organisms.

Microorganisms of the following genera may be mentioned as examples: Alternaria, such as *Alternaria tenuis*, Aspergillus, such as *Aspergillus niger*, Chaetomium such as *Chaetomium globosum*, Coniophora, such as *Coniophora cerebella*, Lentinus, such as *Lentinus tigrinus*, Penicillium, such as *Penicillium glaucum*, Polyporus, such as *Polyporus versicolor*, Aureobasidium, such as *Aureobasidium pullulans*, Sclerophoma, such as *Sclerophoma pityophila* and Staphylococcus, such as *Staphylococcus aureus*.

Depending on their field of use, the active compounds according to the invention can be converted into the customary formulations, such as solutions, emulsions, suspensions, powders, pastes and granules.

These can be prepared in a manner which is known per se, for example by mixing the active compounds with an extender consisting of a liquid solvent and/or solid carriers, if appropriate using surface-active agents, such as emulsifiers and/or dispersing agents, it being possible, for example if extenders are used, optionally to use organic solvents as auxiliary solvents.

Organic solvents for the active compounds can be, for example, alcohols, such as lower aliphatic alcohols, preferably ethanol or isopropanol, or benzyl alcohol, ketones, such as acetone or methylethylketone, liquid hydrocarbons, such as benzine fractions, and chlorinated hydrocarbons, such as 1,2-dichloroethane. The use concentration of the active compounds according to the invention depends on the species and occurrence of the microorganisms to be combated and on the composition of the material to be preserved. The optimum amount to be used can easily be determined by test series. In general, the use concentrations are in the range from 0.001 to 5% by weight, preferably from 0.05 to 2.0% by weight, based on the material to be preserved.

The new active compounds according to the invention can also be mixed with other known active compounds. The following active compounds may be mentioned as examples: benzimidazolyl methyl carbamates, tetramethylthiuram disulphide, zinc salts of dialkyldithiocarbamates, 2,4,5,6-tetrachloro-isophthalonitrile, thiazolylbenzimidazole, mercaptobenzthiazole and phenol derivatives, such as 2-phenylphenol and (2,2'-dihydroxy-5,5'-dichloro)-diphenylmethane.

The active compounds according to the invention can also be used in plant protection as agents for combating pests.

They are employed for example, as fungicidal agents for combating Plasmodiophoromycetes, Oomycetes, Chytridiomycetes, Zygomycetes, Ascomycetes, Basidiomycetes and Deuteromycetes.

The good toleration, by plants, of the active compounds, at the concentrations required for combating plant diseases, permits treatment of above-ground parts of plants, of vegetative propagation stock and seeds, and of the soil.

The active compounds can be converted to the customary formulations, such as solutions, emulsions, suspensions, powders, foams, pastes, granules, aerosols, natural and synthetic materials impregnated with active compound, very fine capsules in polymeric substances and in coating compositions for seed, and formulations used with burning equipment, such as fumigating cartridges, fumigating cans, fumigating coils and the like, as well as ULV cold mist and warm mist formulations.

These formulations are produced in a known manner, for example by mixing the active compounds with extenders, that is, liquid solvents, liquefied gases under pressure, and/or solid carriers, optionally with the use of surface-active agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water; by liquefied gaseous extenders or carriers are meant liquids which are gaseous at normal temperature and under normal pressure, for example aerosol propellants, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly-dispersed silicic acid, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysation products; as dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate can be used in the formulations.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 to 90%.

The active compounds according to the invention can be present in the formulations or in the various use forms as a mixture with other known active compounds, such as fungicides, bactericides, insecticides, acaricides, nematicides, herbicides, bird repellants, growth factors, plant nutrients and agents for improving soil structure.

The active compounds can be used as such or in the form of their formulations or the use forms prepared therefrom by further dilution, such as ready-to-use solutions, emulsions, suspensions, powders, pastes and granules. They are used in the customary manner, for example by watering, immersion, spraying, atomising, misting, vaporising, injecting, forming a slurry, brushing on, dusting, scattering, dry dressing, moist dressing, wet dressing, slurry dressing or encrusting.

In the treatment of parts of plants, the active compound concentrations in the use forms can be varied within a substantial range. They are, in general, between 1 and 0.0001% by weight, preferably between 0.5 and 0.001%.

In the treatment of seed, amounts of active compound of 0.001 to 50 g per kilogram of seed, preferably 0.01 to 10 g are generally required.

For the treatment of soil, active compound concentrations of 0.00001 to 0.1% by weight, preferably 0.0001 to 0.02%, are required at the place of action.

PREPARATION EXAMPLES

EXAMPLE 1

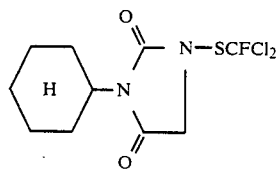

19.4 g (0.106 mol) of 3-cyclohexyl-hydantoin are dissolved in 120 ml of dioxane, with addition of 11 g (0.11 mol) of triethylamine, and 17.7 g (0.105 mol) of dichlorofluoromethanesulphenyl chloride are added dropwise at room temperature. During this addition, the temperature rises to about 45° C. The tert.-amine hydrochloride which has precipitated is filtered off with suction in the cold, the filtrate is concentrated in vacuo and the crude reaction product (33 g) is recrystalised from ethanol. 14 g=42% of theory of 1-(dichlorofluoromethylmercapto)-3-cyclohexyl-hydantoin of melting point 101°-103° C. are obtained.

The following compounds are obtained analogously:

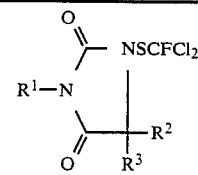

| Example No. | $R^1$ | $R^2$ | $R^3$ | Melting point ($n_D^{20}$) |
| --- | --- | --- | --- | --- |
| 2 | $CH_3$ | H | H | 88–90° |
| 3 | $CH_3$ | $CH_3$ | $CH_3$ | oily |
| 4 | $iC_3H_7$ | H | H | (1.5121) |
| 5 | $nC_4H_9$ | H | H | (1.5182) |
| 6 | $iC_4H_9$ | H | H | 60–64° |
| 7 | $tC_4H_9$ | H | H | (1.5205) |
| 8 | $(CH_3)_3CCH_2$ | H | H | 98–99° |
| 9 | $nC_4H_9$ | $CH_3$ | $CH_3$ | oily |
| 10 | $C_6H_{11}$ | $CH_3$ | $CH_3$ | 73–75° |
| 11 | $C_6H_5CH_2-$ | H | H | 78° |
| 12 | $iC_3H_7$ | $CH_3$ | $CH_3$ | 48–49° |
| 13 | $(CH_3)CCH_2$ | $CH_3$ | $CH_3$ | 59–60° |
| 14 | $C_6H_5CH_2$ | $CH_3$ | $CH_3$ | 67–69° |
| 15 | $C_6H_5CH_2CH_2$ | $CH_3$ | $CH_3$ | 86–88° |
| 16 | $C_6H_5CH_2CH_2$ | $CH_3$ | $CH_3$ | (1.5414) |
| 17 | 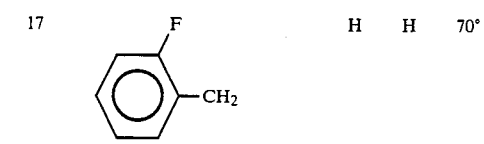 | H | H | 70° |
| 18 | 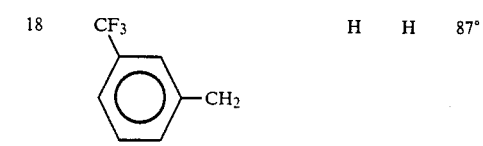 | H | H | 87° |

-continued

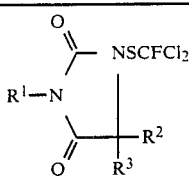

| Example No. | R¹ | R² | R³ | Melting point ($n_D^{20}$) |
|---|---|---|---|---|
| 19 | CF₃–⟨phenyl⟩–CH₂ | H | H | 140° |
| 20 | C₆H₁₁CH₂ | CH₃ | CH₃ | (1.5164) |
| 21 | C₆H₁₁CH₂ | H | H | 68–71° |
| 22 | CF₃–⟨phenyl⟩–CH₂ | H | H | 105–107° |
| 23 | 2-CF₃-phenyl-CH₂ | H | H | 98–99° |
| 24 | norbornyl-CH₂ | H | H | (1.5378) |
| 25 | norbornyl-CH₂ | CH₃ | CH₃ | 88–91° |

USE EXAMPLES

EXAMPLE 26

The minimum inhibitory concentrations (MIC) of active compounds according to the invention are determined to demonstrate the activity against fungi:

Active compounds according to the invention are added in concentration of 0.1 mg/liter to 5,000 mg/liter to an agar prepared from beer wort and peptone. After the agar has solidified, it is contaminated with pure cultures of the test organisms listed in the Table. After storage at 28° C. and 60 to 70% relative atmospheric humidity for 2 weeks, the MIC is determined. The MIC is the lowest concentration of active compound at which no growth at all of the species of microbe used takes place; it is shown in the Table which follows.

TABLE 1

Data of the MIC values in mg/liter for the action of N—sulphenylated hydantoins on fungi

| Test organisms | Test substance according to | | |
|---|---|---|---|
| | Example 3 | Example 5 | Example 10 |
| Alternaria tenuis | 1.5 | 2.0 | 3.5 |
| Aspergillus niger | 10.0 | 50.0 | 20.0 |
| Aureobasidium pullulans | 1.0 | 2.0 | 3.5 |
| Chaetomium globosum | 1.5 | 3.5 | 1.5 |
| Coniophora cerebella | 1.0 | 0.75 | 0.75 |
| Lentinus tigrinus | 1.0 | 0.75 | 0.75 |
| Penicillium glaucum | 50.0 | 100.0 | 75.0 |

TABLE 1-continued

Data of the MIC values in mg/liter for the action of N—sulphenylated hydantoins on fungi

| Test organisms | Test substance according to | | |
|---|---|---|---|
| | Example 3 | Example 5 | Example 10 |
| Polyporus versicolor | 7.5 | 15.0 | 15.0 |
| Sclerophoma pityophila | 5.0 | 5.0 | 5.0 |

EXAMPLE 27

Action against bacteria

The active compounds listed in Table II are added in concentrations of 1 to 5000 ppm to an agar containing bouillon as the nutrient medium. The nutrient medium is then infected with Staphylococcus aureus and the infected medium is kept at 28° C. and 60 to 70% relative atmospheric humidity for 2 weeks. The MIC is the lowest concentration of active compound at which no growth at all of the species of microbe used takes place.

The MIC values are shown in Table II.

TABLE II

Data of the MIC values in mg/liter for the action of N—sulphenylated hydantoins on Staphylococcus aureus

| Test substance according to example | MIC (mg/liter) |
|---|---|
| 3 | 50 |
| 5 | 100 |
| 10 | 50 |

EXAMPLE 28 (Action against slime organisms)

The compounds according to Examples 3, 5 and 10 are each used, dissolved in a little acetone, in concentrations of 0.1 to 100 mg/liter in Allens nutrient solution (Arch. Mikrobiol. 17, 34–53 (1952)), which contains, in 4 liters of sterile water, 0.2 g of ammonium chloride, 4.0 g of sodium nitrate, 1.0 g of dipotassium hydrogen phosphate, 0.2 g of calcium chloride, 2.05 g of magnesium sulphate, 0.02 g of iron chloride and 1% of caprolactam. Shortly beforehand, the nutrient solution is infected with slime organisms (about 10⁶ germs/ml), which have been isolated from spinning water circulations used in the manufacture of polyamide. Nutrient solutions which contain the minimum inhibitory concentration (MIC) or higher concentrations of active compound are still completely clear after culture at room temperature for 3 weeks, that is to say the marked multiplication of the microbes and formation of slime noticeable after 3 to 4 days in nutrient solutions containing no active compound are absent.

TABLE III

Data of the MIC values in mg/liter for the action of N—sulphenylated hydantoins on slime organisms

| Test substance according to example | MIC (mg/liter) |
|---|---|
| 3 | 3 |
| 5 | 5 |
| 10 | 100 |

EXAMPLE 29

Erysiphe test (barley)/protective

Solvent: 100 parts by weight of dimethylformamide
Emulsifier: 0.25 part by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dew-moist. After the spray coating has dried on, the plants are dusted with spores of *Erysiphe graminis* f.sp. hordei.

The plants are placed in a greenhouse at a temperature of about 20° C. and a relative atmospheric humidity of about 80%, in order to promote the development of powdery mildew pustules.

Evaluation is carried out 7 days after the inoculation.

In this test, a clearly superior activity compared with the prior art is shown, for example, by the compounds according to the following preparation examples:

TABLE IV

Erysiphe test (barley)/protective

| Active compound | Active compound concentration in the spray liquor in % by weight | Disease infestation in % of the untreated control |
|---|---|---|
| known: (Captan) [structure: cyclohexene-dicarboximide N—S—CCl$_3$] | 0.025 | 100 |
| according to the invention: [structure with H-cyclohexyl-N, N—SCFCl$_2$] | 0.025 | 0.0 |

EXAMPLE 30

*Fusarium nivale* test (rye)/seed treatment

The active compounds are used as dry dressings. These are prepared by extending the particular active compound with a ground mineral to give a finely pulverulent mixture, which ensures uniform distribution on the seed surface.

To apply the dressing, the infected seed is shaken with the dressing in a closed glass flask for 3 minutes.

2 batches of 100 grains of the rye are sown 1 cm deep in standard soil and are cultivated in a greenhouse at a temperature of about 10° C. and a relative atmospheric humidity of about 95%, in seedboxes which are exposed to light for 15 hours daily.

About 3 weeks after sowing, the plants are evaluated for symptoms of snow mould.

In this test, a clearly superior activity compared with the prior art is shown, for example, by the compounds according to the following preparation examples:

TABLE V

Fusarium nivale test (rye)/seed treatment

| Active compound | Amount of active compound applied in mg/kg of seed | Diseased plants in % of the total plants emerged |
|---|---|---|
| not dressed | — | 12.8 |
| known: (Captan) [structure N—S—CCl$_3$] | 500 | 5.4 |
| according to the invention: [structure H$_3$C—N, N—SCFCl$_2$] | 500 | 0.0 |

EXAMPLE 31

Pyricularia test (rice)/protective

Solvent: 12.5 parts by weight of acetone
Emulsifier: 0.3 part by weight of alkylaryl polyglycol ether To produce a suitable preparation of active compound, 1 part by weight of active compound is mixed with the stated amount of solvent, and the concentrate is diluted with water and the stated amount of emulsifier, to the desired concentration.

To test for protective activity, young rice plants are sprayed with the preparation of active compound until dripping wet. After the spray coating has dried on, the plants are inoculated with an aqueous spore suspension of *Pyricularia oryzae*. The plants are then placed in a greenhouse at 100% relative atmospheric humidity and 25° C.

Evaluation of the disease infestation is carried out 4 days after the inoculation.

In this test, a clearly superior activity compared with the prior art is shown, for example, by the compounds according to the following preparation examples:

TABLE VI

Pyricularia test (rice)/protective

| Active compound | Active compound concentration in % | Disease infestation in % of the untreated control |
|---|---|---|
| known: [structure N—S—CCl$_3$] | 0.025 | 50 |
| according to the invention: | 0.025 | 13 |

TABLE VI-continued

Pyricularia test (rice)/protective

| Active compound | Active compound concentration in % | Disease infestation in % of the untreated control |
| --- | --- | --- |
| ⟨H⟩—N—C(=O)—N—SCFCl₂ (with C=O) | | |

What is claimed is:

1. An N-sulphenylated hydantoin of the formula $$R^1-N\begin{array}{c}C(=O)-NSCFCl_2\\ \\ C(=O)-C(R^2)(R^3)\end{array}$$

in which $R^1$ denotes an optionally substituted $C_1$–$C_{12}$ alkyl, $C_2$–$C_{12}$ alkenyl, $C_5$–$C_{12}$ cycloalkyl, or an aralkyl radical having 6 to 10 carbon atoms in the aromatic part and 1 to 6 carbon atoms in the aliphatic part, substituents being selected from the group consisting of lower alkyl and halogen, and $R^2$ and $R^3$ are identical or different and denote hydrogen, $C_1$–$C_{12}$ alkyl, $C_2$–$C_{12}$ alkenyl or are linked to form a $C_5$–$C_{12}$ cycloalkyl radical.

2. An N-sulphenylated hydantoin according to claim 1, wherein $R^1$ is $C_1$–$C_{12}$ alkyl or $C_5$–$C_{12}$ cycloalkyl.

3. An N-sulphenylated hydantoin according to claim 1, wherein $R^2$ is $C_1$–$C_{12}$ alkyl.

4. An N-sulphenylated hydantoin according to claim 1, wherein $R^3$ is $C_1$–$C_{12}$ alkyl.

5. An N-sulphenylated hydantoin according to claim 2, wherein $R^2$ and $R^3$ are identical or different and denote hydrogen or $C_1$–$C_{12}$ alkyl.

6. An N-sulphenylated hydantoin according to claim 1, wherein said alkyl is a $C_1$–$C_8$ alkyl, said alkenyl is a $C_3$–$C_8$ alkenyl, and said cycloalkyl is a $C_5$–$C_8$ cycloalkyl.

7. An N-sulphenylated hydantoin of the formula $$CH_3-N\begin{array}{c}C(=O)-NSCFCl_2\\ \\ C(=O)-C(CH_3)(CH_3)\end{array}$$

8. An N-sulphenylated hydantoin of the formula $$nC_4H_9-N\begin{array}{c}C(=O)-NSCFCl_2\\ \\ C(=O)-CH(H)\end{array}$$

9. An N-sulphenylated hydantoin of the formula $$⟨C_6H_{11}⟩-N\begin{array}{c}C(=O)-NSCFCl_2\\ \\ C(=O)-C(CH_3)(CH_3)\end{array}$$

10. An N-sulphenylated hydantoin of the formula $$⟨C_6H_{11}⟩-N\begin{array}{c}C(=O)-N-SCFCl_2\\ \\ C(=O)-CH_2\end{array}$$

11. An N-sulphenylated hydantoin of the formula $$H_3C-N\begin{array}{c}C(=O)-N-SCFCl_2\\ \\ C(=O)-CH_2\end{array}$$

12. A microbicidal agent comprising an N-sulphenylated hydantoin according to claim 1 and a diluent.

13. A microbicidal agent according to claim 12, wherein said N-sulphenylated hydantoin is present in an amount of between 0.1 and 95% by weight based upon the weight of said microbicidal agent.

14. A process for protecting a substance against microbial attack which comprises applying to said substance a microbicidally effective amount of an N-sulphenylated hydantoin of claim 1.

15. A process according to claim 14, wherein said substance is an industrial material which can be destroyed by a microorganism.

16. A process according to claim 15, wherein said industrial material is a paint.

17. A process according to claim 14, wherein said substance is a plant.

18. A process according to claim 14, wherein said substance is a plant seed.

19. A process according to claim 14, wherein said substance is a cooling water or cooling lubricant.

20. A process according to claim 14, wherein said substance is wood.

21. A process according to claim 14, wherein said substance is a plant and said plant is rice.

22. A process according to claim 14, wherein said substance is a plant and said plant is a cereal crop.

* * * * *